(12) United States Patent
Sauer (10) Patent No.: US 9,539,119 B2
(45) Date of Patent: Jan. 10, 2017

(54) PROTECTIVE DEVICE PARTICULARLY FOR USE FOR EXTERIOR PROSTHESES

(76) Inventor: Carsten Sauer, Lindlar (DE)

(*) Notice: Subject to any disclaimer, the term of this patent is extended or adjusted under 35 U.S.C. 154(b) by 380 days.

(21) Appl. No.: 12/928,289

(22) Filed: Dec. 8, 2010

(65) Prior Publication Data

US 2011/0131707 A1   Jun. 9, 2011

Related U.S. Application Data (60) Provisional application No. 61/395,525, filed on May 14, 2010.

(30) Foreign Application Priority Data

Dec. 8, 2009   (DE) .................. 10 2009 057 141

(51) Int. Cl.
*A61F 2/78*   (2006.01)
*A61F 2/50*   (2006.01)

(52) U.S. Cl.
CPC .......... *A61F 2/78* (2013.01); *A61F 2002/5001* (2013.01); *A61F 2002/5089* (2013.01)

(58) Field of Classification Search
USPC ... 602/3, 5, 20, 23; 128/846, 877–879; 2/16, 2/59, 61
See application file for complete search history.

(56) References Cited

U.S. PATENT DOCUMENTS 4,098,268 A * 7/1978 Scott .................. A61F 15/004
                                             128/DIG. 20
4,363,317 A * 12/1982 Broucek ..................... 602/3

(Continued)

FOREIGN PATENT DOCUMENTS

AT       E 61 218 B    12/1991
DE       17 89 684     11/1958
(Continued)

OTHER PUBLICATIONS

With DryPro® Prosthetic Cover Amputees Enjoy the Beach and Water Without Worry, News Release and Product Information, DryCorp, Mar. 17, 2009 (3 pages).

*Primary Examiner* — Ophelia A Hawthorne
(74) *Attorney, Agent, or Firm* — Hudak, Shunk & Farine Co. LPA (57) ABSTRACT

People who wear a prosthesis currently have to use a bathing prosthesis if they wish to pursue water sports or take a shower or reach a body of water for recreational purposes and take active part in beach pursuits safely. However, these are usually taken off for swimming though this is very often not possible in the case of rocky shores or unsupervised beaches, quite apart from the unwelcome attention to which the person wearing the prosthesis is sometimes exposed in doing so. To solve this problem, a protective device for use for exterior prostheses is suggested, in which the protective device is a protective covering made from an at least semi-elastic, durable and damage resistant material being watertight or custom-designed sufficiently preventing a penetration of water into the inside of the protective covering and being dimensionally conformed to the shape of the body, and at least one end of which is furnished with a cuff or sleeve or collar like semi-elastic device that is dimensionally adapted to the contours of the anatomy of the person wearing the protective covering to prevent water or moisture or foreign bodies from penetrating the protective covering. This is particularly convenient and easy to carry and use when travelling and for recreational sport.

3 Claims, 4 Drawing Sheets

(56) References Cited

U.S. PATENT DOCUMENTS

| | | | |
|---|---|---|---|
| 4,768,501 A | | 9/1988 | George |
| 5,133,775 A | | 7/1992 | Chen |
| 5,439,438 A | * | 8/1995 | Ersfeld et al. ............... 602/3 |
| 5,593,453 A | * | 1/1997 | Ahlert ........................ 623/27 |
| 5,680,653 A | * | 10/1997 | Mathis et al. ............... 2/123 |
| 5,769,809 A | * | 6/1998 | Witzel ........................ 602/62 |
| 5,807,290 A | * | 9/1998 | Barry .......................... 602/3 |
| 6,126,621 A | * | 10/2000 | Aceves ........................ 602/3 |
| 7,913,320 B2 | * | 3/2011 | Grissom ...................... 2/59 |
| 2004/0215118 A1 | * | 10/2004 | Dumas et al. ............... 602/3 |
| 2009/0182252 A1 | * | 7/2009 | Bennett ...................... 602/3 |

FOREIGN PATENT DOCUMENTS

| | | |
|---|---|---|
| DE | 1789684 U | 6/1959 |
| DE | 100 40 955 A1 | 3/2002 |
| DE | 100 40 995 A1 | 3/2002 |
| DE | 20 20 916 U1 | 5/2002 |
| DE | 201 20 916 U1 | 5/2002 |
| EP | DE 41 25 635 A1 | 2/1993 |
| WO | 00 51531 A1 | 9/2000 |

* cited by examiner

PROTECTIVE DEVICE PARTICULARLY FOR USE FOR EXTERIOR PROSTHESES

FIELD OF THE INVENTION

The invention relates to a protective device for use for exterior prostheses, where the protective device is dimensionally conformed to the shape and size of the body or adapted to the contours of the anatomy of the person wearing the protective device, respectively.

BACKGROUND OF THE INVENTION

Exterior prostheses in the form of arm and leg prostheses are known in the art. They are made particularly from metals and/or carbon or other plastics and fibre materials. However, these materials do not lend themselves especially well to being worn when showering or pursuing water sports, because water, and particularly salt water, can attack and damage the very valuable, expensive materials of the prosthesis. Therefore, it is known to use "bathing prostheses". These are made from plastics, but they do not have the advantages of the valuable metal or carbon prostheses, either with regard to wearing comfort or handling, the person who is wearing the bathing prosthesis can take a shower with it on or use it to walk to a body of water for recreation. It can even be worn for brief periods in the water, to cool down. But the disadvantage remains in that it usually must be removed for swimming and left on the bank at the point of entry into the water. In this context, the further problem arises in that in the case of rocky shores or unsupervised beaches, this is often not possible. Moreover, as the person in question removes the prosthesis, his handicap becomes evident to third parties and accordingly draws irritating attention to him. Since the design of such bathing prostheses usually is relatively unsophisticated, the prosthetic-wearing person is also prevented from getting to bodies of water that can only be reached by walking over rocks, stones and paths, because such routes usually do not offer a secure purchase.

Tubes are also known that are made from thin material and may be tightened on one side with a rubber drawstring or similar. In order to be able to adapt these to the anatomical shape of the person wearing the prosthesis or plaster cast, underpressure is created inside the tube. A valve and pumping bulb are provided in the skin of the tube for this purpose or another kind of device for producing an underpressure. Such a solution for sealing casts is especially known from AT 61218 E or from products of the company Dry Corp., LLC under the name Dry Pro™. Alternatively, it is known to use heat to fit it closely to the body of the person wearing the prosthesis or cast in the manner of a shrink tube. In either of these cases, the result is not very appealing. Moreover, if a valve with pumping bulb is provides, the problem arises that the valve may be damaged or opened during use later, and the sealing effect will be lost. In addition, swimming in bodies of water is rendered awkward because of the excessive amount of material. The short service life of these tubes or shrink tubes represents a further problem, since they can become damaged and start to leak very easily. In case of breakdown or malfunction of the valve or damage of the tube, respectively, an excessive amount of water will penetrate into the inner of the tube within a very short time. Moreover, the shrink tube variant can only be used once, and takes a great deal of effort to remove afterwards. This variant is thus a disposable product which is difficult to take off after use.

DE 41 25 635 A1 discloses a cover for a femoral or shank prosthesis and a method for producing the same wherein the cover is made of an elastic material with a closely tight surface such that the cover is watertight and water absorption is prevented. The cover is tube-like with a shape adapted to the limbs to be replaced. It can be fastened to the respective parts of the prosthesis with its both opening portions spaced from one another. Thus, only the prosthesis is watertightly sealed such that in principal some kind of bathing prosthesis is provided on the basis of a regular prosthesis. The transition from the upper prosthesis edge to the skin of the person wearing the prosthesis is, however, not watertight or protected against the penetration of water into the inside the cover or the prosthesis, respectively, such that water can penetrate into the same. Without the outside sealing the material of the cover is not watertight but will absorb water, since here a regular textile is pulled over the prosthesis and is sealed.

U.S. Pat. No. 5,593,453A discloses a prosthesis cover of a watertight latex material which closely conforms to the shape of the limb being covered. On the inner surface the cover has an anti-friction inner surface. Further, the cover has an anti-skid sole in the case of a leg cover. The anti-skid surface is provided with a plurality of inwardly directed ribs formed on the inner surface of the leg portion of the cover, the plurality of ribs being spaced apart from each other with each rib extending concentrically of the leg portion. The plurality of ribs extends from just above an ankle portion throughout the height of the leg portion to just an upper segment to space the cover from the prosthesis and to thereby reduce the frictional engagement when the cover is being applied by sliding over the prosthesis. At the outside the cover has finger loops for enabling the pulling on and off which finger loops will negatively affect the aesthetic of the cover and cannot provide the impression of a human skin.

The object of the present invention is therefore to overcome the problems mentioned with regard to the known protective devices and to create a device to replace both the bathing prosthesis and vacuum or shrink tubes as well as the above mentioned protective devices which enables the wearer to shower and swim safely, and to participate fully in beach life actively and without attracting undue attention, wherein the penetration of water and foreign bodies, respectively, like sand, dirt, dust, into the inside of the protective device can securely be prevented.

SUMMARY OF THE INVENTION

The object is solved for a protective device for use for exterior prostheses in that the protective covering is made from an at least semi-elastic, waterproof or watertight or custom-designed sufficiently preventing water from penetrating the inside of the protective covering resilient and durable and damage-resistant material, and has a cuff or sleeve or collar like at least semi-elastic device at one end thereof the dimensions of which are adapted to the contours and size of the anatomy of the person wearing the protective covering to prevent water or moisture or foreign bodies from penetrating into the protective covering. Refinements and advanced embodiments of the invention are defined in the dependent claims.

Accordingly, a protective device for use for exterior prostheses is created that is worn as a protective covering over a conventional prosthesis. In this way, it serves as protection therefore, since it is thus possible to effectively prevent water and foreign bodies from penetrating the prosthesis and, thus, damaging the prosthesis by penetrating water or penetrating foreign embodiments, like especially sand, can be effectively avoided. The term watertight means waterproof and splash water resistant and water resistant as well as moisture proof. The feature of a custom-designed sufficient obviation of a penetration of water into the protective covering means that dependant on the respective use the protection by the material of the protective device as well as the protective device itself is made such that the entrance of water or moisture into the protective device can be avoided. The material of the protective device thereby is watertight, the construction of the protective device as well as its treatment especially with regard to the connection area of the material is custom-designed or with regard to the respective use avoids the penetration of water into the protective device. Hereby, especially splash water but also water during a shower or bathing can be prevented from entering the inside of the protective device. Therefore, the cuff or sleeve or collar like at least semi-elastic device is provided which provides a secure bearing of the protective device on the skin of the person wearing the prosthesis by optimally adapting its shape to the body part next to the prosthesis where the protective covering holds tightly on. By this shape adapting combined with the at least semi-elasticity the protective device adheres optimally onto the skin of the person wearing the protective device. The protective covering according to U.S. Pat. No. 5,593,453 A only has a conically shaped upper end portion which is, however, made as one part with the rest of the protective covering. No cuff or sleeve or collar like device is, thus, added contrary to the present invention, where the device is made of a material providing a very good bearing on the extremity stump which device is made of at least semi-elastic material. So, the prosthesis is optimally protected against damages by the material of the protective covering and the prosthesis is further optimally protected against damages by penetration of water, moisture, foreign bodies etc. by the sleeve or collar of cuff like at least semi-elastic device attached to the rest of the protective covering such that the device and the rest or main body of the protective covering can be made of optimal materials each being attached to one another. Thus, the prosthesis is optimally protected in every aspect.

By the use of an at least semi-elastic material, that is to say a material of which at least a part has elastic properties, and which is adapted to the contours of the body, the protective device fits closely, at least at the pertinent points, against the extremity stump to which the prosthesis is attached, and possibly also against the prosthesis, so that the protective device remains in the desired position, this alone helping to prevent penetration at least by dirt such as dust, but also by sand. The dimensional conformation to the shape of the body is understood to mean dimensional conformation to the anatomy of a person, not necessarily a specific person, but generally to the shape and size of human bodies. Mass production is possible in this context, but so is individual adaptation to a specific person, of course. In mass production, the protective device may offered in various sizes, reflecting the differing anatomies of people, some of whom may be taller or stouter, according to the same principle that is applied for clothing in different sizes. In this way, an adaptation to the body of the person wearing the protective device may also be made visually, which represents an aesthetic advantage over the tubes of the prior art, which cannot be adjusted dimensionally to the body shape, but are instead significantly oversize, and accordingly hang over the anatomical shape of the person like a cloth, particularly in the area of a person's arm or leg, after shrinking or removal of the air.

Using a durable, damage-resistant material helps to prevent cracks from forming when the protective device is used, which would allow water and foreign bodies to enter the inside of the protective device. A durable, damage-resistant material is understood to be material that is relatively tear-resistant, and thick enough not to rip for example if it scrapes on stones or other hard objects in passing. In this context, durable means that the material is capable of withstanding stresses without suffering any, or at least essentially any damage, particularly without ripping. In this context, damage-resistant particularly means that the material may only be separated by deliberate cutting, but is otherwise stable enough to protect the person wearing the protective device from the entry of moisture or foreign bodies. Watertight non hydrophilic materials such as chloroprene rubber, polychlorophene rubber or chlorobutadiene rubber, thus, foamed rubber materials, have proven to be particularly suitable for this purpose. Latex material is not understood to be a damage-resistant or durable material. The materials mentioned in the prior art, such as latex, do not show the desired stability and durability. Especially an easy moving and sporting at the beach or any gardening is not possible with these kinds of protective devices. Further, the protective devices according to the prior art may not be combined with bathing shoes worn over the protective devices. This means an essential disadvantage since the normal prosthesis has an ankle which is always set in a specific angle dependent on the desired heel height. Without a shoe the leg may be brought automatically and inadvertently into a hyper extended position. In such a position someone can do swimming without any problems. When he wants to run or walk this is not possible without any risk when he does not wear shoes which wearing of shoes is possible with the protective device according to the present invention and which is, however, not possible with the protective devices according to the prior art as cited above. Walking or running along the beach, especially sporting, as well as gardening is, thus, not possible without any difficulty with protective devices according to the prior art.

Of special advantage is a cuff or sleeve or collar like device which is added to the material provided for the rest of the extension of the protective device which is, thus, added as a sleeve or collar to the end side of the protective device. By this cuff or sleeve or collar like device it is possible to provide the inner surface of the cuff or sleeve or collar like device directed to the inside of the protective device with an adhesive effect or with an adhesive, respectively. A penetration of humidity or moisture or water is securely avoided by use of the sleeve or collar like device. The device is furnished with an opening. This is usually at least the opening through which the wearer slides the protective device on, that is to say the end of the protective device that subsequently lies against the extremity stump. Since the device is dimensioned so as to conform to the wearer's anatomy, it fits particularly closely against the extremity stump, which already helps to prevent water and foreign bodies, especially dust, from getting into the protective device.

The cuff or sleeve or collar like device may include a long-lasting elastic material with adhesive effect, particularly latex and/or silicone, and/or a material having a smooth surface with adhesive property. Simply by virtue the material's elasticity, as already mentioned, the cuff or sleeve or collar like device already lies very close against the wearer's skin adjacent to the prosthesis, which also provides good protection against penetrating moisture but also against the entrance of dust. Unlike a shrink tube, the protective device may also be removed very easily after use, and may, thus, be used repeatedly.

As has been described, the protective device is made at least in part from a chloroprene rubber, polychloroprene rubber or chlorobutadiene rubber. The side of the chloroprene, polychloroprene or chlorobutadiene rubber that is intended to lie against the skin of the wearer may be provided in the end or side area or in the area of the sleeve or collar like device of the protective device, which is shaped so as to cover the prosthetic wearer's skin, with a smooth surface having adhesion properties, designed as smooth skin Neoprene® for example. Providing such a border or selvage or designing the device with such cuffs that are attached to rest of the material of the protective device also serves as a further measure for preventing water from getting inside the protective device when this border or cuff or sleeve or collar like device fits tightly against the skin of the person wearing the prosthesis.

The device shaped as a selvage or shaped as an attached sleeve or collar having a wedge of silicone or latex may be provided to create good grip on the skin of a person wearing the protective device. The device also may be made of silicone or latex material. Since the device advantageously has an adhesive effect, thus an adhesive or gluing effect, a very good and tight sticking on the skin surface of a person is possible by such an adhesive effect.

To achieve particularly good waterproofing and a much better sticking on the skin surface of a person, in this area, a skin adhesive may be applied to the smooth border area of the protective device that has adhesive properties, i.e. the cuff like or sleeve like or collar like device. This may be a liquid or have the form of a double-sided adhesive tape or another form of an adhesive. It is applied to the end on the inside of the protective device that is designed as the protective covering, in other words the side intended to contact the person's skin, where an opening is provided for putting on and taking off the protective covering. When the protective covering is shaped like a long stocking for protecting a leg prosthesis, the device and the skin adhesive are advantageously provided in the area in which the protective covering is in contact with the prosthetic wearer's skin.

Alternatively to applying skin adhesive, or possibly in addition to such application, a separate, cuff-like covering element made from a waterproof material or a material preventing the penetration of water, particularly silicone and/or latex, may be provided. This may cover both the border area of the protective device and the skin of the person wearing the protective device, thus providing protection against penetration particularly by moisture and water and dust. A material having an adhesive effect can be printed e.g. to the outside of the cuff or sleeve or collar like device provided at the end of the protective device, so that a watertight connection is possible by overlapping the sleeve or collar like device by the cuff-like element. Thus, attaching the protective device to the skin of the prosthetic wearer adhesively or providing the cuff-like element in this way helps to reliably prevent water and foreign bodies from getting inside the protective device, even while pursuing various types of water sport. Providing a latex or silicone cuff to form the end of the protective device's border, that is to say either as a border edge or sleeve or collar like device previously attached to the protective device or as a separate covering element, is able to create a waterproof attachment to a person's skin even without using a skin adhesive.

The unfurling effect of the end side boarder area, thus the boarder portion, or the cuff of sleeve or collar like device during the wearing by a person can be avoided by sticking the device to the person's skin. Further, it is possible to provide the device with at least one device preventing the unfurling movement. The same can be built as at least one pocket like unfurling preventing device with at least one stick like reinforcing insert. The pocket like unfurling preventing device can be applied onto the material of the protective device, e.g. in the form of an ironed material patch, when provided as a rubber material or being applied adhesively or in another way when coated with an adhesive material. For providing a stiffening or reinforcing effect in order to avoid any unfurling movement of the edge or boarder portion of the protective device at least one reinforcing insert is inserted, e.g. in the form of a stick, in the pocket like unfurling preventing device. By the subsequent inserting it is possible to withdraw the reinforcing insert for cleaning the pocket like unfurling preventing device. Alternatively, it is possible to provide at least one reinforcing device which is not removably fixed onto the material of the protective device.

Here it should be emphasized that the providing of a skin adhesive, of a separate cuff like covering element or of an unfurling preventing device advantageously provides additional components which are not necessary for the protective device. By use of these additional components the water tightness may be increased for specific cases of operation or use, where larger forces impact the protective device and result in a releasing effect of the protective device with regard to the skin surface of the person wearing the same. This effect may for example appear during diving or if the body shape in the area of the extremity stump of the person wearing the protective device is distinctively conical.

It is further advantageous if the protective device is constructed in multiple layers. In this case, the protective device may include at least one foam layer, for example a layer of foam chloroprene rubber, polychloroprene rubber or chlorobutadiene rubber. To ensure a sturdy, easy to handle surface, at least one side of the protective device is also furnished with a surface coating, in particular it is laminated. Such a surface coating or lamination may be provided on one or both sides, that is to say on the outside and/or the inside of the protective device. In all cases it is also possible not to provide any surface coating or lamination. Suitable materials for such surface lamination particularly include lycra and nylon, which are particularly applied as a woven surface.

The selvage or the sleeve or collar like device of the protective device may be made from a chloroprene rubber, polychloroprene rubber or chlorobutadiene rubber, which may be laminated or unlaminated. This is advantageously made from smooth skin Neoprene® on the side facing towards the person wearing the protective device, and in this context it has a lamination on one side and is unlaminated on the other side and has a smooth surface of chloroprene rubber, polychloroprene rubber or chlorobutadiene rubber to show the intended adhesive effect directed to the skin of the person wearing the protective device. If a selvage or a sleeve or collar like device, respectively, of silicone and/or latex is provided, this advantageously has the form of a cuff in solid material. If technically possible, the cuffs may also be laminated on the side facing away from the person wearing the protective device. The device for protecting against wet and moisture and for preventing penetration by dust, sand and dirt may thus have the form either of a cuff made particularly from the materials described above and be connected to the rest of the material of the protective device or affixed thereto, or it may be conformed directly with the rest of the material of the protective device or fitted onto it.

The abutting points of the protective device material may be essentially sealed to make them watertight, particularly by sewing, welding or adhesion. A mixture of these joining methods is also easily possible, The material used to manufacture the protective devices may have a material thickness from 0.5 mm to 5 mm, for example, particularly from 1 to 3 mm. This lends the protective device very good stability combined with sufficient but not excessive rigidity, while still retaining all possible dimensional stability. When a thin material is used for the protective device, that is to say precisely with chloroprene rubber, polychloroprene rubber or chlorobutadiene rubber, such material may be butt welded and the weld seam may be covered with corresponding strips. In this way, the abutting points may be rendered sufficiently waterproof and durable even when a thinner material is used. Besides the foam layer, other material layers may also be provided, which are joined together one on top of the other to create the material of the protective device. For example, the outer layers may also be provided using materials that are highly abrasion-resistant and for example resistant to seawater.

In addition, at least one material or material patches that increase friction may be provided on the sole area of a foot, ensuring good grip when the wearer is walking over rocks or other slippery surfaces. The sole is thus rendered non-slip by design, particularly by coating.

The sealed construction of the protective device itself and its close fit against the skin of the person wearing the prosthesis, particularly if no adhesion is applied there and no separate cuff-like covering element is used, serves to effectively keep out of the protective device's inside not only water, but also sand and dust of course, thus also successfully preventing the prosthesis from being damaged. Accordingly, it is not necessary to use additional waterproofing means or means to prevent dust and sand from getting in.

The protective device may be designed in the manner of a sleeve or legging with integral hand or foot element. It is also possible to design the protective device as a tubular arm or leg covering without a hand or foot element. If the hand or foot element is created integrally with the protective device, particularly secure protection is provided against penetration by water or moisture, since then only one opening must be securely closed and sealed. In the case of a tubular protective device that has however been adapted dimensionally to fit the person wearing it, and in which the hand or foot of the person wearing the prosthesis protrudes out of the protective device, two openings are provided in the protective device, and these are located and particularly secured by adhesion at the wrist or ankle, that is to say in the area of the hand or foot of the person wearing the prosthesis, and in the area of the shoulder or thigh or hip of the person wearing the prosthesis.

The protective device may also be designed as a one-legged trouser-like covering incorporating the form of the body part or the torso of the person wearing the protective device. Such a design is particularly suitable for people who only have very short stumps in the area of their extremity, making it almost impossible to affix the protective device securely there. For this purpose, the protective device is then designed as a trouser-like covering of a covering incorporating the form of the torso, so that it may be affixed elsewhere on the body and not at the extremity stump. In this case too, an adhesive material or skin adhesive or a respective cuff or sleeve or collar like device may be applied to the respective openings where water or moisture, or also dust and sand might enter, in order to provide waterproofing or at least to make it difficult for water, moisture, dust, sand and foreign bodies to get in.

In terms of appearance, the protective device may be adapted to the normal skin colour of the wearer, or it may be coloured differently. Contrary to the prior art this is possible and will lead to a result having a very good appearance. Conventional methods such as silk-screen printing, or also lacquering and airbrushing may be used to colour the material. The natural colour of a laminating material, which may be in a variety of colours, may also be used on the side of the protective device that faces outwards, that is to say away from the wearer. The material used for the protective device may also be dyed in all cases.

The protective devices may be cut into shaped panels from a chloroprene rubber, a polychloroprene rubber or chlorobutadiene rubber, and subsequently joined at their abutting points, for example by sewing, adhesion or welding. The lamination or coating is applied to the base material or along the abutting points of the material panels of the sleeve and legging shapes where applicable before joining. A coating may be or may have been applied to both sides or also to just one side, so that in the finished legging or sleeve shapes a coating is provided only on the outside, or only on the inside, of on both the outside and the inside, by placing another material layer over the top of it, or laminating over it. The material specification or design, that is to say its colour, the material used one-sided or double-sided lamination or coating, one-sided smooth surface and so on, may be incorporated in the base material, that is to say in the yard goods or when the panels are cut. One layer of a foam chloroprene rubber, polychloroprene rubber or chlorobutadiene rubber for example, such as are marketed under the Neoprene® brand by DuPont for example, is provided as the middle layer in a multilayer construction of the protective device. However, it may also be prepared as the only layer. Accordingly, the possible construction variants are such having only one semi-elastic and essentially water impermeable material layer, such having a lamination or coating only on the outside, that is to say facing away from the person wearing the protective device, such having a lamination or coating only on the inside, that is to say facing towards the person wearing the protective device, and such having both an inner and outer coating or lamination. A solid material mad from a material having adhesive properties, such as latex or silicone, may be provided for the selvages or cuffs. The base material of the protective device may also be designed with a smooth surface on the inside, facing towards the person wearing the protective device, in which case in particular an outer lamination or coating may also be provided. Not only the base material, but also the selvages or cuffs or sleeve or collar like devices may be prefabricated and merely cut to size according to the intended application before they are joined to the rest of the protective device material.

In the case of injured limbs, water sports and visits to the beach are avoided to protect the wound from exposure to moisture and dirt. To enable the injured person to actively participate in beach activities, and even pursue water sports despite this, a protective device for protecting limbs against contact with moisture, and particularly foreign bodies such as dirt, includes furnished with a protective covering made from an at least semi-elastic, water impermeable or custom-designed sufficiently preventing the inside of the protective device from the penetration of water, resilient and damage-resistant material and that has been adapted to conform to the body size and shape and at least one end of which is equipped with a cuff-like, sleeve like or collar like device having a size and anatomically conformed shape for preventing penetration by water or moisture and foreign bodies. The devices may be or have been constructed in the same way that the device described previously for protecting an exterior prosthesis.

The present protective device thus has the advantage with regard to known bathing prostheses in that it is very much smaller and easier to handle, which is a significant advantage, particularly when travelling. An extra bathing prosthesis does not need to be included in luggage, only the small, folding protective device, which fits into luggage like any normal item of clothing. Moreover, it is not necessary to bring a pumping bulb or a heat radiating device for shrinking protective devices so that they lie flush against the wearer's skin, and this is also an important advantage over the tube-like protective devices according to the prior art, which are only available in standard sizes. These advantages may be enjoyed not only when travelling but during any other leisure activities, particularly in recreational sport, since here too the protective device may be carried in a sports bag much more easily than other protective devices, such as bathing prostheses above all but also such tube-like devices that must be shrunk or require means for creating a vacuum. Also with regard to the other above mentioned protective devices according to the prior art the protective device according to the present invention is more comfortable during use, thus, also during its pulling on and off as well as during maintenance and cleaning. Also, any necessary repairs can be done much easier since on one hand the multilayer material can be better repaired and on the other hand the cuff or sleeve or collar like device can be much easier and better changed or repaired when being deteriorated or damaged because of the attachment of the cuff or sleeve or collar like device to the rest of the protective device.

DESCRIPTION OF THE DRAWINGS

In the following text, embodiments of the invention will be described in greater detail, with reference to the drawing for detailed explanation thereof.

In the drawing.

DETAILED DESCRIPTION OF THE INVENTION

Figure 1A:
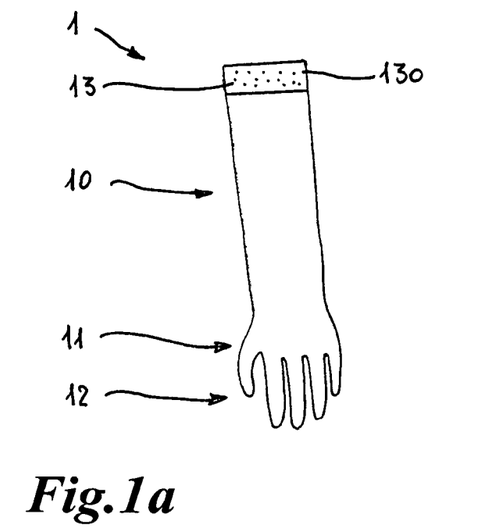
FIG. 1a is a side view of a first embodiment of a protective device according to the invention for use for arm prostheses.
Figure 1B:
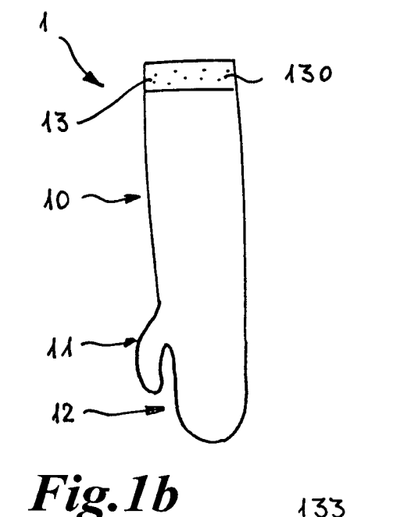
FIG. 1b is a side view of a variant of the embodiment of the protective device of FIG. 1a, FIG. 2a is a side view of a second embodiment of a protective device according to the invention for use for an arm prosthesis.

FIGS. 1a and 1b show embodiments of a protective device 1 in the form of a "sleeve", that is to say a protective covering for an arm prosthesis. The protective device is furnished with an arm section 10 and a hand section 11 with a finger section 12, which is shown fully with clearly illustrated fingers in the embodiment in FIG. 1a, but only indicated or reproduced as a mitten in the embodiment in FIG. 1b. The finger section covers the fingers of the hand prosthesis like a glove, just as the hand section of protective device 1 covers the rest of the hand prosthesis. The arm section covers both the arm portion of the prosthesis and a part of the extremity stump of the person wearing the prosthesis, that is to say it fits closely against the skin. This close fitting against the skin occurs at least at the upper arm end area 13. At least the inside of this area is provided with an adhesive material or consists of such an adhesive material to provide watertightness and ensure a good grip in this area. For example, protective device 1 has a cuff or sleeve or collar like device 130, for example in the form of an affixed cuff in upper arm end area 13. It can be made from latex and/or silicone. Another smooth surface having adhesive properties may also be provided here directed to the extremity stump, thus, on the inside of the protective device 1 or the cuff or sleeve or collar like device 130. If a material other than latex and/or silicone is used for upper arm end 13, if necessary a wedge-shaped insert or an insert made from latex and/or silicone may be provided and this significantly increases grip on the extremity stump and skin of a person wearing the protective device. Otherwise, the material of the protective device or the cuff or sleeve or collar like device 130 has a degree of elasticity at least in the area of the arm section adjacent to the upper arm end and in the upper arm end area so that it is able to lie particularly snugly and tight against the extremity stump, and is able to create a tight closure against the skin of the person wearing the prosthesis.

Figure 2A:
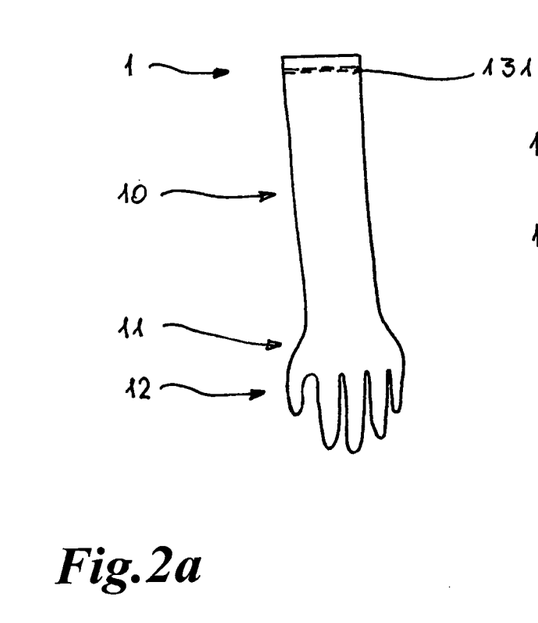
Figure 2B:
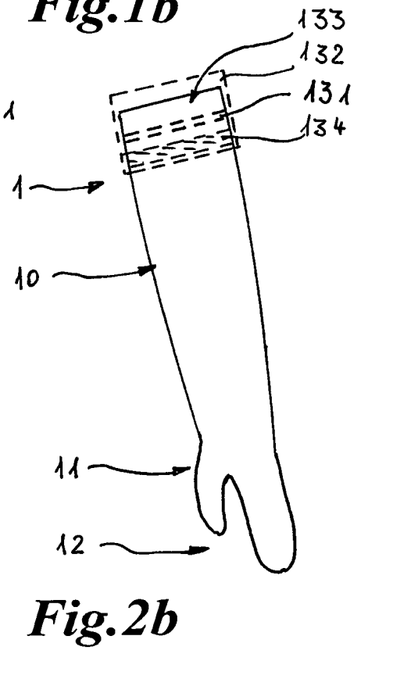
FIG. 2b is a side view of a variant of the embodiment of the protective device of FIG. 2a, FIG. 3 is a side view of an embodiment of a protective device according to the invention for use for a leg prosthesis.

FIGS. 2a and 2b show a second embodiment of a protective device 1 in the form of a sleeve, this embodiment being very similar in principle to the embodiment shown in FIGS. 1a and 1b. Unlike that embodiment, however, the protective device 1 of FIGS. 2a and 2b does not have an upper arm end with affixed latex and/or silicone. Instead, inside of the upper arm end in the form of a cuff or sleeve or collar like device 130, facing towards the person wearing the protective device, is provided with a smooth surface having adhesive properties, particularly produced from a smooth skin Neoprene®. The upper arm end may be attached to the rest of the material of the protective device or it may be produced as an integral part thereof. In order to ensure waterproofing when lying on the skin of a person wearing the protective device 1, a skin adhesive 131 may additionally be applied to the smooth surface, which already has inherent adhesive properties, thus enabling a particularly secure and tight connection with the skin of the person wearing the sleeve. This variant is used particularly when smooth skin Neoprene® is provided, but it may be used equally well with an attached silicone cuff. A silicone material can advantageously be used especially for people who react on latex material or are allergic with regard to latex material. It should be noted that an additional waterproof seal is assured by just a latex or silicone cuff such that no further means are necessary for providing a protection against the penetration of water, especially in case of a desired splash water protection.

Instead of a skin adhesive, a cuff-like covering element 132 may be pulled over the selvage of the protective device and the wearer's skin to provide good protection against penetration by moisture and water and dust or dirt. Such a covering element is shown in FIG. 2b by broken lines. For a specific watertight connection the protective device may be provided with an adhesive material in the area of the upper arm and on the outside 133, e.g. in the form of a printing 134. This is indicated in FIG. 2b.

For use for a right and left arm, either the same protective devices 1 or correspondingly adapted, differently conformed protective devices may be provided. Coatings may be provided to improve anti-slip characteristics particularly on the palm, and optionally in the area of the finger sections. This enables the person wearing the prosthesis to support himself on the prosthetic hand if necessary without fear of slipping over, particularly on wet and therefore slippery surfaces.

Figure 3:
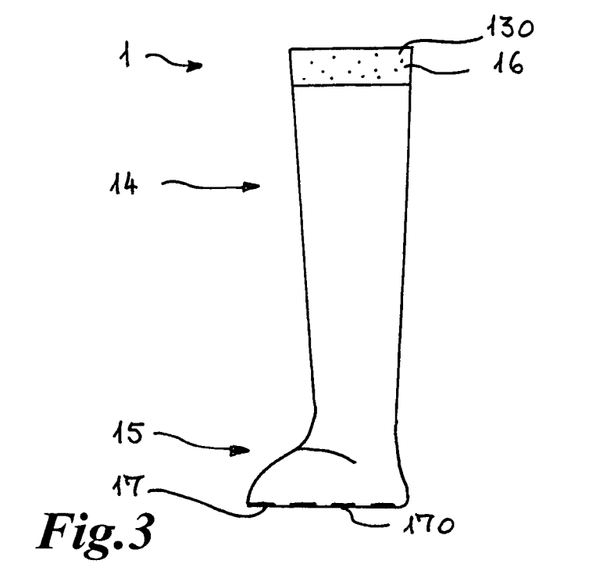

FIG. 3 shows protective device 1 in the form of a "legging" for pulling over a leg prosthesis. This protective device is designed analogously with protective device 1 shown in FIGS. 1a and 1b, but is provided with a leg section 14 and a foot section 15. Instead of an upper arm end 13, hear a thigh end 16 is provided, which also ensures protection against penetration by water and foreign bodies, if necessary even without use of a skin adhesive. For this purpose, the thigh end also has a surface having adhesive properties in the area of the cuff or sleeve or collar like device 130. This consists in particular of a long-lasting elastic material with adhesive effect. As for upper arm end 13, thigh end 16 may also often be realised as a separate element and attached to leg section 14 or arm section 11. Thigh end 16 is made for example from latex and/or silicone or it has a corresponding insert made from latex and/or silicone. It is also possible to apply an adhesive coating or lamination to the thigh end or upper arm end in the area of the cuff or sleeve or collar like device 130 on the side thereof facing the skin of the wearer, or to use a material with corresponding adhesive properties, particularly smooth skin Neoprene®.

Figure 4:
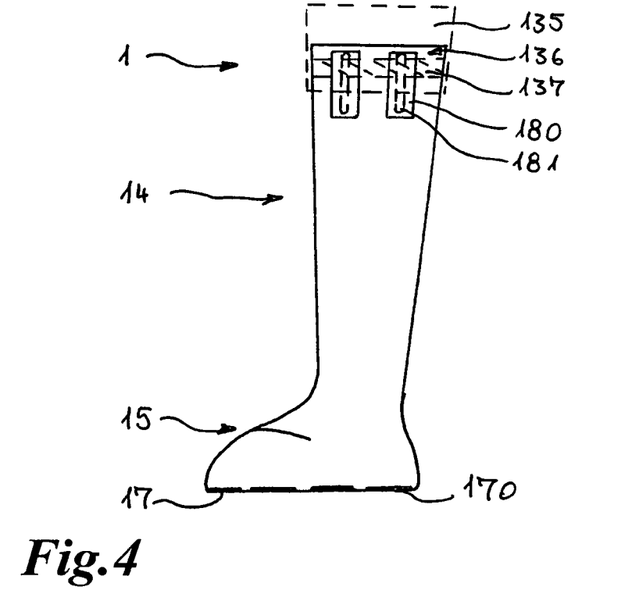
FIG. 4 is a side view of a further embodiment of a protective device according to the invention for use for a leg prosthesis.

Such an alternative embodiment to the embodiment of a legging of FIG. 3 is shown in FIG. 4. The legging shown here differs from the embodiment of FIG. 3 only in that a smooth surface having adhesive properties, particularly a smooth skin Neoprene®, is provided in the thigh end area or the area of the cuff or sleeve or collar like device as an inner surface, that is to say facing towards the person wearing the protective device. The thigh end may be attached to the rest of the material of the protective device as a cuff, or it may be produced integrally therewith. Is for the embodiment of FIGS. 2a and 2b, a skin adhesive is also used here, ensuring a much better watertightness when it is applied to the skin of the person wearing the prosthetic. Otherwise, watertightness may also be assured simply by providing a wedge insert made from latex and/or silicone. A further alternative to this embodiment consists in providing a separate cuff-like covering element 135, made from latex and/or silicone for example. This is pulled over the border of the protective device and over the skin of the person wearing the protective device, and is thus able to prevent particularly moisture and water and dust and dirt from penetrating the protective device as just mentioned above with regard to FIGS. 2a and 2b. Like there an additional sealing by for example printing an adhesive material onto the outside 136 of the protective device in the form of a printing 137 in the area of the thigh end is possible here (at least indicated in FIG. 4). To avoid an unfurling of the thigh end a number of pocket like unfurling preventing devices 180 with rod or stick like reinforcing inserts 181 is applied there. The reinforcing inserts 181 can be removed for cleaning such that the pocket like unfurling preventing devices 180 are open at one side. They can also be totally closed such that the removing of the reinforcing inserts is no longer possible. The reinforcing inserts 181 can also be directly applied to the material of the protective device in the area of the thigh end, for example they can be sewn on or stitched in there. However, no removing of the sticks or rods is possible then.

In the embodiments of the protective device shown in FIGS. 3 and 4, both soles 17 of the two leggings may be furnished with an anti-slip coating 170. Particularly on wet and slippery surfaces, this is able to provide better grip for the prosthesis wearer.

Figure 5:
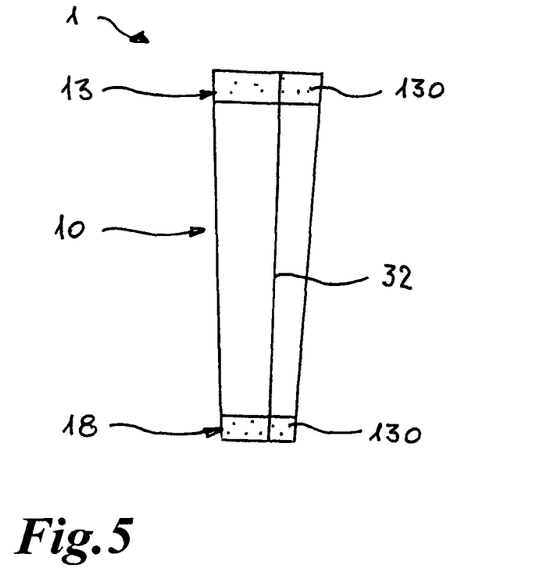
FIG. 5 is a side view of a seventh embodiment of a protective device according to the invention for use for an arm prosthesis.

Since the sleeves in FIGS. 1a, 1b and 2a, 2b are each shown with an attached or integral hand section 11 and finger section 12, the hand and finger sections of protective device 1 are not shown in FIG. 5. This protective device is simply tube-shaped like arm section 10. However, this embodiment also has an upper arm end 13 with a cuff or sleeve or collar like device 130 exactly like the embodiment of FIG. 1. In addition, a wrist end 18 is also provided in the wrist area of the arm prosthesis to create a seal. As before, upper arm end 13 is advantageously made from a long-lasting elastic material with adhesive effect, particularly latex and/or silicone or provided with a material having adhesive effect and optionally a skin adhesive to create a seal sealing against the penetration of water with the skin of the person wearing the prosthesis. Since wrist end 18 lies flush with the prosthesis surface, so that the prosthetic hand is uncovered, a sealing end is created with the surface of the prosthesis in the area of wrist end 18, and a long-lasting elastic material with adhesive effect may be advantageously used here too.

Figure 6:
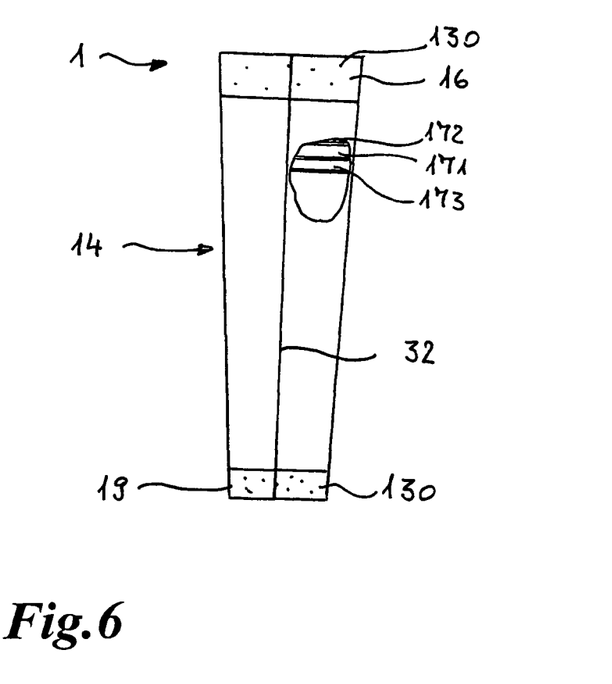
FIG. 6 is a side view of an eighth embodiment of a protective device according to the invention for use for a leg prosthesis.

FIG. 6 shows a corresponding legging design without a foot section. In this case, the prosthetic foot of the person wearing the this prosthesis is uncovered, and the legging has an ankle end 19 in the area of the ankle of the prosthesis. Thus, protective device 1 as shown in FIG. 6 only includes one leg section 14 with a thigh end 16 at one end, and accordingly there are two openings, which are in watertight contact with the skin of the person wearing the prosthesis and also with the prosthesis itself. Here too, long-lasting elastic materials with an adhesive effect may be provided, particularly as a solid material, for example latex and/or silicone, in the area of the thigh end and the ankle end, in the form of cuff or sleeve or collar like devices 130.

The two opposite ends of both the sleeve of FIG. 5 and the legging of FIG. 6 may also be provided only with a smooth surface having at least a small amount of adhesiveness, and may be affixed to the skin or the surface of the prosthesis in watertight manner by adhesion with the aid of a skin adhesive. However, the provision of an adhesive material that is able to function without the use of an adhesive is more suitable, particularly in the area close to the prosthesis, since the adhesive would have to be removed from the prosthesis without causing it any damage when the protective device is removed. Accordingly, the use of materials, such as latex and silicone, for example, which have inherent adhesive qualities, and which can be removed from the surface of the prosthesis without residue and without attacking the prosthesis, is advisable. For this reason, a cuff-like covering element made from latex and/or silicone that is arranged to cover the respective selvage of the protective device and the uncovered prosthesis is most suitable.

Figure 7:
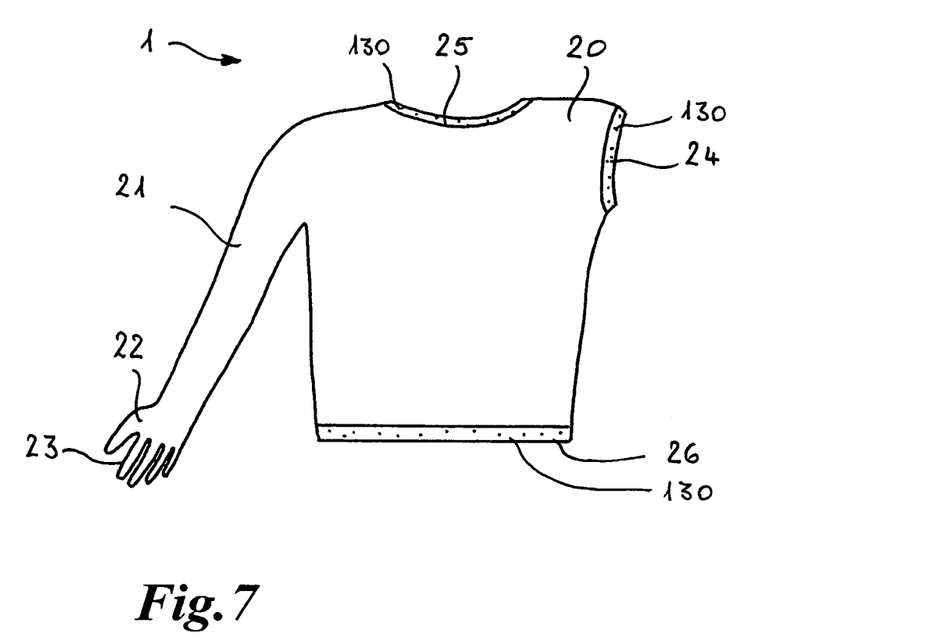
FIG. 7 is a side view of a ninth embodiment of a protective device according to the invention for use for an arm prosthesis, in the form of a protective covering that incorporates the upper body.

FIG. 7 shows a further embodiment of a protective device 1, which in this example is configured as a protective covering incorporating the upper body. This example is similar in shape to a pullover in which the sleeve on one side is conformed to a hand section, but there is no second sleeve. Thus, protective device 1 has a torso section 20, an arm section 21 and a hand section 22 with finger section 23. The arm prosthesis arranged on the side of arm section 21, hand section 22 and finger section 23 may thus be fully covered and protected. Especially when the extremity stump is too short to allow a protective device to be attached securely here, attachment is assured in such manner that very good attachment to the body of the person wearing the prosthesis is possible via torso section 20. The healthy arm protrudes through a corresponding arm opening 24 in the torso section. Torso section 20 is also furnished with a neck opening 25 and a bottom opening 26 facing towards the abdomen. Cuff or sleeve or collar like devices or elements for protecting against penetration by water, moisture and dirt are advantageously provided in the area of these three openings 24 to 26, particularly a long-lasting elastic material having an adhesive effect on at least one side, such as smooth skin Neoprene® or latex or silicone as solid materials, wherein material coatings or laminations having adhesive properties may be applied to another material. It is also possible to use for example a chloroprene rubber, polychloropene rubber or chlorobutadiene rubber with a smooth, adhesive surface, in which case a skin adhesive may be applied additionally here as well to provide a watertight seal in the area of openings 24 to 26.

Figure 8:
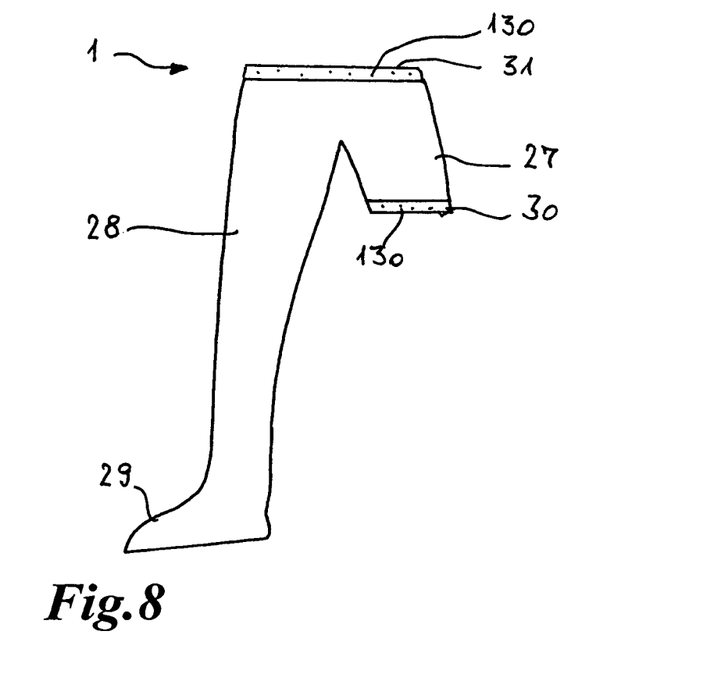
FIG. 8 is a side view of a tenth embodiment of a protective device according to the invention for use for a leg prosthesis, in the form of a trouser-like protective covering.

FIG. 8 shows a corresponding counterpart to the embodiment for the arm prosthesis in the form of a protective device 1 constructed in the manner of a single trouser leg for a leg prosthesis. One leg of this trouser-like protective device is then designed in the manner of a pair of tights, while the other only extends with a thigh section 27 over a portion of the healthy thigh of a person wearing a one-sided leg prosthesis. The leg prosthesis is accommodated completely in the leg section 28 conformed in the manner of one half of a pair of tights. The leg section is also furnished with a foot section 29. In this manner, it is possible to fully enclose the leg prosthesis, thus ensuring reliable protection for the leg prosthesis even if the extremity stump is too short at the thigh to allow a protective device as shown in FIG. 3 or 4 to be attached securely thereto.

The two remaining openings 30, 31 in the thigh section and in the area of the thigh of the person wearing the protective device may also be conformed variously to provide a watertight seal, and in particular cuff or sleeve or collar like devices 130 made of a long-lasting elastic material having adhesive properties and having a smooth surface with adhesive properties may be provided, and may optionally be affixed to the skin surface of the person wearing the protective device using a skin adhesive. It is also possible to provide for example a cuff made from latex and/or silicone.

A design that is conformed to the body shape of the person wearing the protective device is particularly advantageous especially in the embodiments shown in FIGS. 7 and 8, since when the material is lying very closely against the person's skin, the desired sealing effect may be assured, and the person is also not impeded unnecessarily by the protective device.

Many other shapes may be created besides those shown, particularly also combination shapes of the variants illustrated. In particular, the two embodiments of FIGS. 7 and 8 may also be realised without a hand section or a foot section respectively, that is to say they may be equipped correspondingly with a wrist end or ankle end. In any case, it is advantageous to provide a secure attachment to the body of the person wearing the prosthesis in order to protect the valuable prosthesis from damage, particularly caused by penetrating dust, sand and water, especially seawater. An injured arm or leg may also be protected from contact with moisture and foreign bodies by a protective device of such kind.

Chloroprene rubber, polychloroprene rubber or chlorobutadiene rubber, particularly in the foam forms, are suitable materials for the protective device, and the material of the protective device may also be created using multiple layers as indicated e.g. in FIG. 6. In this case the layer 171 of foam material may be provided particularly effectively as the inner material layer, while other material layers 172, 173 having greater resistance to wear are arranged above and below it. Layers of such kind may be made from lycra and/or nylon or other wear-resistant materials. The cut material panels are joined by sewing, adhesion, welding, or by some other process to form a sealed protective device. A seam 32 of such kind is indicated in FIGS. 5 and 6. The surface of the protective device may be dyed, in particular to match the skin colour of the individual wearing the prosthesis. A lamination or coating may also be coloured. It is even possible to simulate body hair with colouring methods.

Besides the embodiments described above of protective devices for use for exterior prostheses, many other embodiments may also be created, in which the protective device in each case is a protective covering made from an at least semi-elastic, watertight or essentially watertight, or resistant to water penetration or splash water or waterproof, durable, tear-resistant and damage-resistant material that is dimensionally conformed to the shape of the body, and at least one end of which is furnished with a cuff or sleeve or collar like at least semi-elastic device the dimensions of which are conformed to the body shape of the person wearing the protective device so that water or moisture and foreign bodies are unable to penetrate. The elastic device especially adheres to the person's skin and prevents penetration of water or moisture or dirt or dust, respectively, or foreign bodies into the inside of the protective device.

While in accordance with the patent statutes, the best mode and preferred embodiment have been set forth, the scope of the invention is not limited thereto, but rather by the scope of the attached claims.

REFERENCE NUMERALS

1 Protective device
10 Arm section
11 Hand section
12 Finger section
13 Upper arm end
14 Leg section
15 Foot section
16 Thigh end
17 Sole
18 Wrist end
19 Ankle end
20 Torso section
21 Arm section
22 Hand section 23 Finger section
24 Arm opening
25 Neck opening
26 Lower opening
27 Thigh section
28 Leg section
29 Foot section
30 Opening
31 Opening
32 Seam
130 cuff or sleeve or collar like device
131 Skin adhesive
132 covering element
133 outside
134 printing with adhesive material
135 covering element
136 outside
137 printing
170 Anti-slip coating
171 layer of foamed material/inner material layer
172 upper material layer
173 lower material layer
180 pocket like unfurling preventing device
181 stick rod like reinforcing insert

What is claimed is:

1. A protective device for use for exterior prostheses, wherein the protective device consisting of a protective covering dimensionally conforming to a body size and shape and wherein the protective covering is made from a material being at least semi-elastic, durable, damage-resistant, watertight or custom-designed sufficiently preventing water from penetrating an inside of the protective covering, wherein at least one end of the protective covering is furnished with a cuff-shape or sleeve-shape or collar-shape at least semi-elastic device having dimensions which prevent penetration by water or moisture or foreign bodies into the inside of the protective covering, wherein the cuff-shape or sleeve-shape or collar-shape at least semi-elastic device consists of a single layer of material having an inner side with an adhesive property.

2. The protective device as recited in claim 1, wherein the cuff-shape or sleeve-shape or collar-shape at least semi-elastic device is made at least in part from one or more of the materials chloroprene rubber, polychloroprene rubber, and chlorobutadiene which materials have a smooth surface having adhesion properties, and wherein the protective covering comprises chloroprene rubber, polychloroprene rubber or chlorobutadiene rubber.

3. The protective device as recited in claim 2, wherein the protective device is constructed as a sleeve or legging incorporating a hand or foot element.

* * * * *